(12) United States Patent
Li (10) Patent No.: US 10,305,039 B2
(45) Date of Patent: May 28, 2019

(54) MATERIAL PROPERTY TESTING DEVICE AND MANUFACTURING METHOD FOR THE SAME

(71) Applicant: Wuhan China Star Optoelectronics Semiconductor Display Technology Co., Ltd., Wuhan, Hubei (CN)

(72) Inventor: Songshan Li, Guangdong (CN)

(73) Assignee: Wuhan China Star Optoelectronics Semiconductor Display Technology Co., Ltd., Wuhan, Hubei (CN)

( * ) Notice: Subject to any disclaimer, the term of this patent is extended or adjusted under 35 U.S.C. 154(b) by 0 days.

(21) Appl. No.: 15/556,065

(22) PCT Filed: Jul. 21, 2017

(86) PCT No.: PCT/CN2017/093824
§ 371 (c)(1),
(2) Date: Sep. 6, 2017

(87) PCT Pub. No.: WO2019/000519
PCT Pub. Date: Jan. 3, 2019

(65) Prior Publication Data
US 2019/0006594 A1    Jan. 3, 2019

(51) Int. Cl.
*H01L 51/00* (2006.01)
*H01L 27/32* (2006.01)
*H01L 51/56* (2006.01)
*G01N 21/25* (2006.01)

(52) U.S. Cl.
CPC ....... *H01L 51/0031* (2013.01); *G01N 21/255* (2013.01); *H01L 27/322* (2013.01); *H01L 27/3246* (2013.01); *H01L 27/3248* (2013.01); *H01L 51/0018* (2013.01); *H01L 51/56* (2013.01); *G01N 2201/0621* (2013.01)

(58) Field of Classification Search
CPC .......................... H01L 51/0031; G01N 21/255
See application file for complete search history.

(56) References Cited

U.S. PATENT DOCUMENTS 8,872,244 B1 * 10/2014 He .......................... H01L 29/78
257/288
2017/0077194 A1   3/2017 Liu et al.

FOREIGN PATENT DOCUMENTS

| CN | 105529409 A | 4/2016 |
| CN | 106898710 A | 6/2017 |
| CN | 206225365 U | 6/2017 |

(Continued)

*Primary Examiner* — Thomas L Dickey
(74) *Attorney, Agent, or Firm* — Andrew C. Cheng (57) ABSTRACT

A material property testing device and a manufacturing method are disclosed. The device includes: a substrate; a metal gate electrode; an auxiliary layer disposed on the metal gate electrode, and the metal gate electrode is located between the substrate and the auxiliary layer; a function layer disposed on the substrate. In the formation process of the function layer, an organic photoresist is attached on the auxiliary layer for a period of time, and the function layer is used for cooperating with a light-emitting device to test the property of the material. A film of the organic photoresist being disposed is even such that after exposing and developing, the function layer having an ideal pattern is obtained so as to ensure the testing effect of the material property testing device.

12 Claims, 5 Drawing Sheets

(56) References Cited

FOREIGN PATENT DOCUMENTS

| JP | 2009070708 A | 4/2009 |
|----|--------------|--------|
| JP | 2015142277 A | 8/2015 |

* cited by examiner

MATERIAL PROPERTY TESTING DEVICE AND MANUFACTURING METHOD FOR THE SAME

BACKGROUND OF THE INVENTION

1. Field of the Invention

The present invention relates to a material property testing technology, and more particularly to a material property testing device and manufacturing method for the same.

2. Description of Related Art

The LED (Light-Emitting Diode) has been widely applied in many industries. Along with the development of the technology, the OLED (Organic Light-Emitting Diode) and the WOLED (White Organic Light-Emitting Diode) appear successively. Currently, the LED, OLED and WOLED have been widely applied in many industries including indication light or applied in desk lamp, TV, display panel, and monitor. Therefore, the luminous effect of the LED is very important.

In the manufacturing process of LED, OLED and WOLED, a pixel definition material is required. The performance of the material directly affects the luminous effect of the LED, OLED and WOLED, specifically, the oxygen content and water content of the material. Therefore, the pixel definition material applied in the LED, OLED and WOLED is required to be tested.

In the process for manufacturing a material property testing device, a metal gate electrode is firstly formed through exposing, developing and etching. Then, through exposing and developing to form a color filter layer and/or an insulation layer on the substrate in order to cooperate to test the pixel definition material. In the formation process of the color filter layer and/or insulation layer, an organic photoresist is required to be coated on the substrate and the metal gate electrode in order to form a film. Then, through exposing and developing to remove the extra organic photoresist on the metal gate electrode and the substrate in order to leave a useful portion to form the color filter layer and/or the insulation layer. Because the adhesion force of the organic photoresist on the metal is poor, the organic photoresist film is usually broken. Accordingly, an uniformity of the organic photoresist film is affected such that the pattern of the color filter layer and/or the insulation layer formed after exposing and developing is not ideal, and greatly affecting the testing effect of the testing device.

SUMMARY OF THE INVENTION

To improve the poor adhesion force of the organic photoresist on the metal gate electrode of the conventional material testing device, and bad pattern of the color filter layer and/or the insulation layer after exposing and developing, the present invention provides a material property testing device and manufacturing method for the same.

The present invention provides a material property testing device for testing a property of a material, comprising: a substrate; a metal gate electrode disposed at a side of the substrate; an auxiliary layer disposed at a side of the metal gate electrode away from the substrate, wherein, the auxiliary layer includes a first body and a second body, the first body is disposed on the side of the metal gate electrode away from the substrate, and the second body is disposed on a side of the substrate having the metal gate electrode; and a function layer including a color filter layer and being disposed on the side of the substrate having the metal gate electrode, the second body is located between the function layer and substrate, in the formation process of the function layer, an organic photoresist is attached on the auxiliary layer for a period of time, and the function layer is used for cooperating with a light-emitting device to test the property of the material.

The present invention also provides a manufacturing method for a material property testing device, comprising steps of: providing a substrate; depositing a layer of metal material on the substrate, through exposing, developing and etching to obtain a metal gate electrode; depositing a layer of auxiliary material on the substrate and the metal gate electrode, through exposing, developing and etching to obtain an auxiliary layer on the metal gate electrode; and coating a layer of an organic photoresist material on the substrate and the metal gate electrode, and forming a function layer on a side of the substrate having the metal gate electrode through exposing and developing.

The material property testing device and manufacturing method for the same of the present invention forms an auxiliary layer on the surface of the metal gate electrode, and the auxiliary layer is a nonmetallic material. Therefore, in the process of manufacturing the function layer, the organic photoresist is deposited on the substrate and the auxiliary layer. Because the adhesion force of the organic photoresist on the auxiliary layer is strong, the organic photoresist film being deposited is even, a function layer having an ideal pattern is obtained so as to ensure the testing effect of the material property testing device.

DETAILED DESCRIPTION OF THE PREFERRED EMBODIMENT

The following will combine the figures to describe a material property testing device and a manufacturing method for the same in detail.

Figure 1:
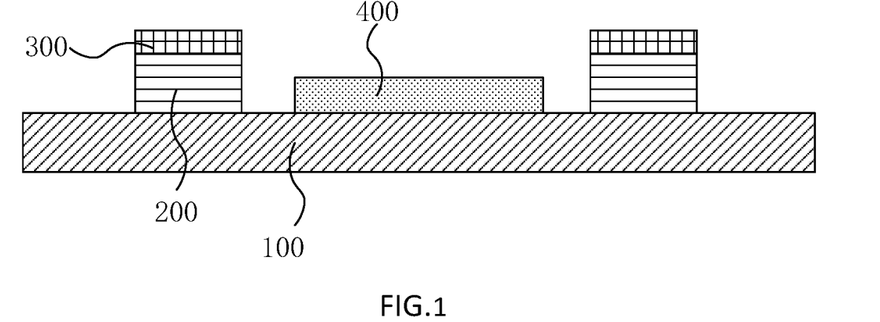
FIG. 1 is a schematic diagram of a material property testing device according to an embodiment of the present invention.

With reference to FIG. 1, and FIG. 1 is a schematic diagram of a material property testing device according to an embodiment of the present invention. The material property testing device includes a substrate 100, a metal gate electrode 200 disposed at a side of the substrate 100, an auxiliary layer 300 disposed at a side of the metal gate electrode 200 away from the substrate 100, and a function layer 400 disposed at a side of the substrate 100 having the metal gate electrode 200.

Specifically, the metal gate electrode 200 is located between the substrate 100 and the auxiliary layer 300. The metal gate electrode 200 is used for electrically connecting another part. The function layer 400 is made of an organic photoresist material for cooperating with a light-emitting device to test a property of a material. In the formation process of the function layer 400, the organic photoresist is attached on the auxiliary layer 300 for a period of time.

Specifically, the process that the function layer 400 is formed on the substrate 100 is: the organic photoresist is coated on the substrate 100 and the auxiliary layer 300; then, through different exposure amount, removing an excess portion of the organic photoresist on the metal gate electrode 200 and the substrate 100 in order to remain an useful pattern to form the function layer 400. As shown in FIG. 1, in the above solution, in the formation process of the function layer 400, at the location of the metal gate electrode 200, the organic photoresist is coated on the auxiliary layer 300, and the organic photoresist is not directly contacted with the metal gate electrode 200. Because an adhesion force of the organic photoresist on the auxiliary layer 300 is strong, a film of the organic photoresist being disposed is even such that after exposing and developing, the function layer 400 having an ideal pattern is obtained so as to ensure the testing effect of the material property testing device.

Preferably, the metal gate electrode 200 is located on the substrate 100 and located closed to an edge of the substrate 100, and the function layer 400 is located at a middle of the substrate 100.

Preferably, the substrate 100 can be a transparent glass substrate or a quartz substrate.

It can be understood that the auxiliary layer 300 is a non-metallic layer. Preferably, the auxiliary layer can be SiNx or SiOx with a single layer, or a mixture of SiNx and SiOx, or one layer of SiNx and a combination of one layer of SiOx and one layer of SiOx.

Figure 2:
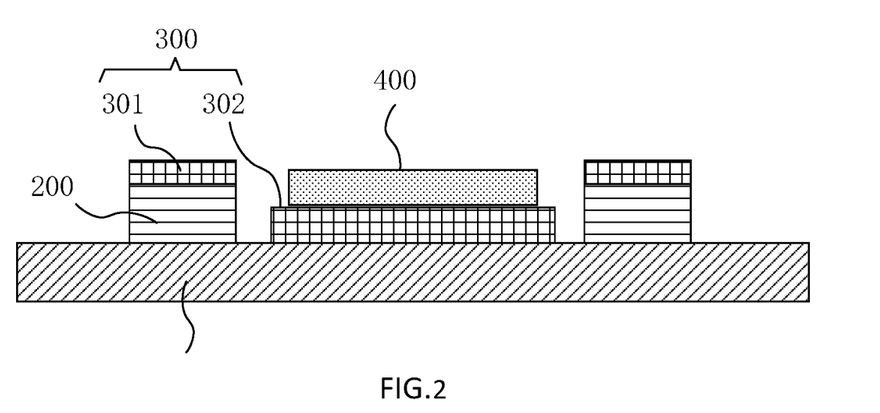
FIG. 2 is a schematic diagram of a material property testing device according to another embodiment of the present invention.

With reference to FIG. 2, in one embodiment, the auxiliary layer 300 includes a first body 301 and a second body 302. The first body 301 is disposed on a side of the metal gate electrode 200 away from the substrate 100, and the second body 302 is disposed on a side of the substrate 100 having the metal gate electrode 200. The second body 302 is located between the function layer 400 and substrate 100. Because an adhesion force of the organic photoresist on the auxiliary layer 300 is strong, the second body 302 disposed on the substrate 100 can ensure that in the forming process of the function layer, the organic photoresist can be evenly coated such that the function layer 400 having an ideal pattern is obtained so as to ensure the testing effect of the material property testing device.

The operation principle of the material property testing device in testing the material is: forming a material to be tested in the material property testing device, and connecting the material to be tested with a light-emitting device. The light-emitting device emits light to the substrate 100. If the luminous effect is ideal (mainly considering the color, brightness and clarity of the emitting effect), the property of the material to be tested is good.

Figure 3:
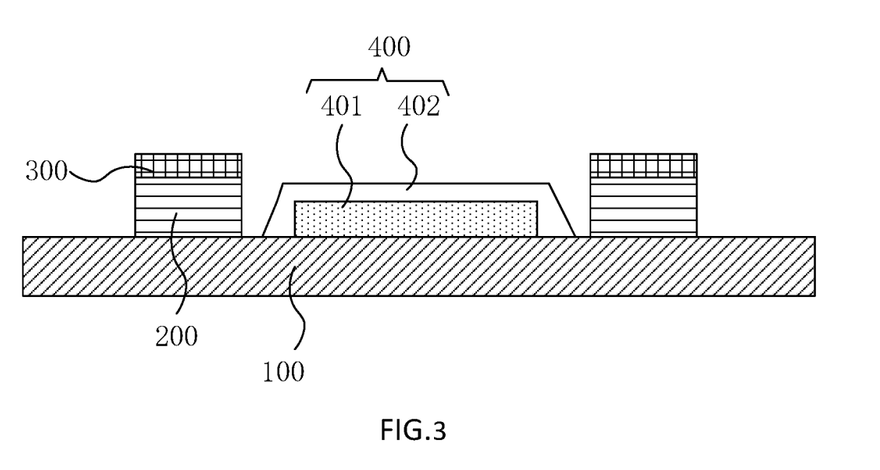
FIG. 3 is a schematic diagram of a material property testing device according to another embodiment of the present invention.

With reference to FIG. 3, preferably, the function layer 400 includes a color filter layer 401. The color filter layer 401 mainly has a light filtering function. If a light emitted from the light-emitting device is white such as a WOLED, the color filter layer 401 is required to cooperate with the light-emitting device such that through the color filter layer 401, the white light is decomposed into a color light in order to observe the luminous effect. Specifically, the color filter layer 401 is made of acrylic resin.

In another embodiment, the function layer 400 further includes an insulation layer 402, the color filter layer 401 is located between the substrate 100 and the insulation layer 402. The insulation layer 402 has an insulation and isolation function. In a normal situation, if the color filter layer 401 is connected with a part that is connected with the metal gate electrode 200, the filtering effect of the color filter layer 401 will be affected, and an operation process of the part connected with the metal gate electrode 200 will also be affected. Accordingly, disposing the insulation layer 402 on the color filter layer 401 can ensure that the operation performance of the part connected with the metal gate electrode 200 and the color filter layer 401 can work properly. Preferably, the insulation layer 402 is made of polyimide and/or acrylic material.

Figure 4:
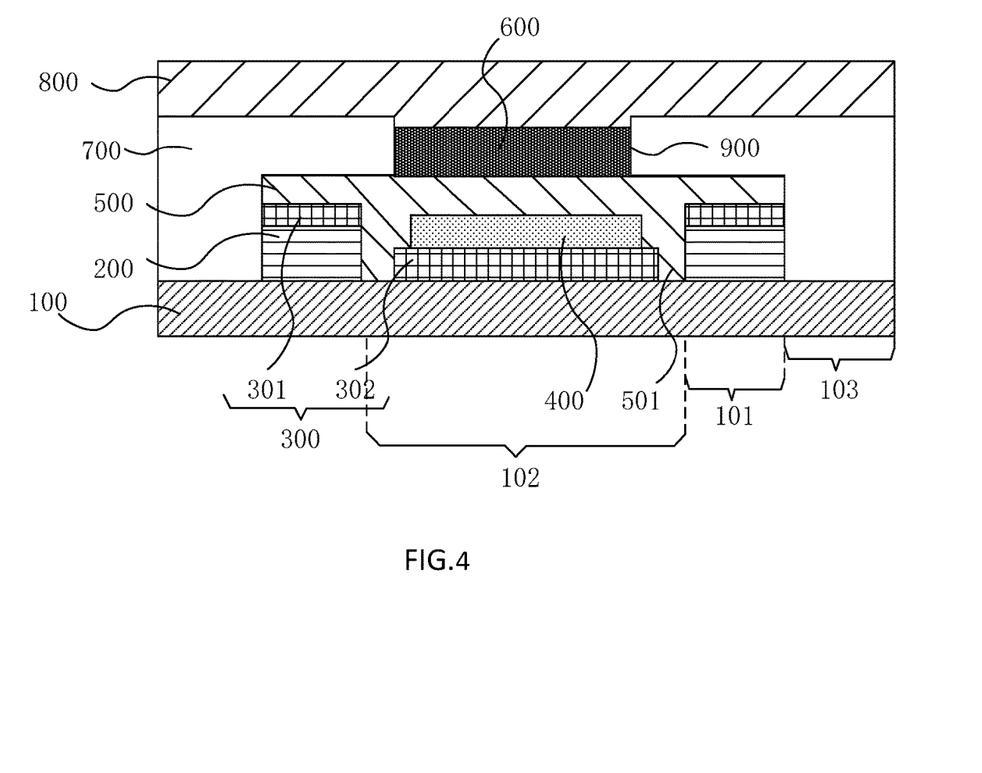
FIG. 4 is a schematic diagram of a material property testing device according to another embodiment of the present invention.

With reference to FIG. 4, in one embodiment, the material property testing device further includes an anode layer 500, a material layer to be tested 700, a light-emitting material layer 600 and a cathode layer 800. Wherein, the anode layer 500 is electrically connected to the metal gate electrode 200. The material layer to be tested 700 is located between the anode layer 500 and the cathode layer 800. Besides, the material layer to be tested 700, the anode layer 500 and the cathode layer 800 commonly form a cavity 900 for receiving the light-emitting material layer 600. The light-emitting material layer 600 is received in the cavity 900, and the light-emitting material layer 600 abuts the material layer to be tested 700. The following will describe the operation principle of the material property testing device in the present embodiment. The metal gate electrode 200 is connected with an external power source (not shown in the figure). Then the power is delivered to the anode layer 500 such that between the anode layer 500 and the cathode layer 800, a voltage difference is formed and the voltage difference is applied on the light-emitting material layer 600 so that the light-emitting material layer 600 emits a light, and the light acts on the substrate 100 in order to observe the light-emitting effect. Because the material layer to be tested 700 abuts the light-emitting material layer 600, the material layer to be tested 700 will directly affect the luminous effect of the light-emitting material layer 600. Accordingly, from the luminous effect of the light-emitting material layer 600, the property of the material layer to be tested 700 is inspected.

In the present embodiment, the metal gate electrode 200 is divided into two pieces. On the substrate 100, the substrate 100 is divided into a metal region 101, a middle region 102 and a peripheral region 103. The function layer 400 is also formed on the substrate 100, and located at the middle region 102 between two pieces of metal gate electrode 200. The anode layer 500 is located at the metal region 101 and the middle region 102, and the anode layer 500 covers the auxiliary layer 300, a portion of the substrate 100 at the middle region 102 and the function layer 400. The light-emitting layer 600 is located at the middle region 102 and is formed in the anode layer 500. The cathode layer 800 is located at the metal region 101, the middle region 102 and the peripheral region 103. The light-emitting layer 600 is located between the anode layer 500 and the cathode layer 800. The material layer to be tested 700 is located at the peripheral region 103, the metal region 101 and a portion of the middle region 102. At the peripheral region 103, the material to be tested 700 is located between the substrate 100 and the cathode layer 800. At the metal region 101 and a portion of the middle region 102, the material layer to be tested 700 is located between the anode layer 500 and the cathode layer 800. The above structure can ensure that an exterior structure of the product to be tidy in order to simplify the manufacturing process. It can be understood that in another embodiment, the cathode layer 800 can only be formed at the middle region 102, the only requirement is to ensure that between the anode layer 500 and the cathode layer 800, a voltage difference can be formed to provide to the light-emitting material 600. In another embodiment, at least a portion of the material layer to be tested 700 is formed between the cathode layer 800 and the anode layer 500, and abuts the light-emitting material layer 600.

Specifically, at the anode layer 500, an extension body 501 is provided to be electrically connected to the metal gate electrode 200. In the present embodiment, the extension body 501 is connected with a side surface of the metal gate electrode 200. At this time, the auxiliary layer 300 only includes a first body 301 disposed above the metal gate electrode 200, or the second body 302 disconnected with the first body 301 in order to leave a space at the side of the metal gate electrode 200 for receiving the extension body 501 of the anode layer 500 in order to realize an electric connection between the anode layer 500 and the metal gate electrode 200.

Figure 5:
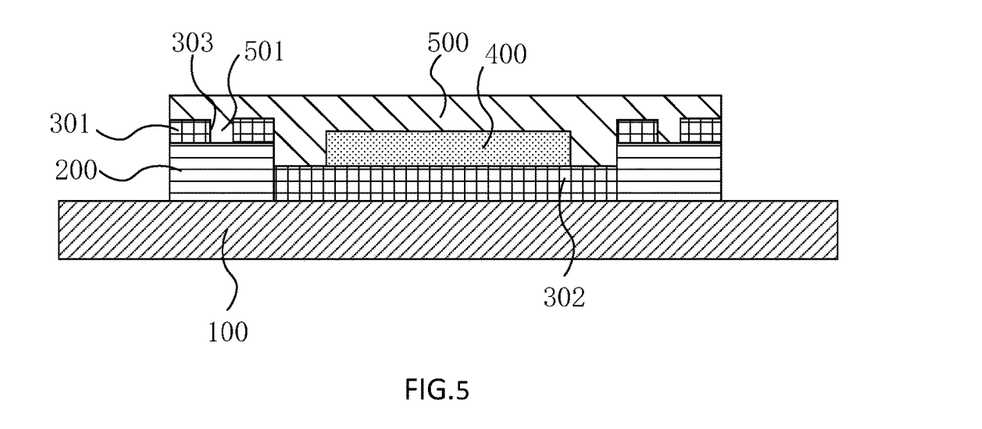
FIG. 5 is a schematic diagram of an auxiliary hole according to an embodiment of the present invention.

With reference to FIG. 5, in another embodiment, the first body 301 is provided with an auxiliary hole 303 communicating with the metal gate electrode 200. The extension body 501 abuts the metal gate electrode 200 through the auxiliary hole 303 in order to realize an electric connection between the anode layer 500 and the metal gate electrode 200.

In the material property testing device of the present invention, through forming the auxiliary layer 300 on the metal gate electrode 200, in the forming process of subsequent function layer 400, at the location of the metal gate electrode 200, the organic photoresist is coated on the auxiliary layer 300, and the organic photoresist is not directly contacted with the metal gate electrode 200. Because an adhesion force of the organic photoresist on the auxiliary layer 300 is strong, a film of the organic photoresist being disposed is even such that after exposing and developing, the function layer 400 having an ideal pattern is obtained so as to ensure the testing effect of the material property testing device.

The present invention also provides with a manufacturing method for a material property testing device.

Figure 6:
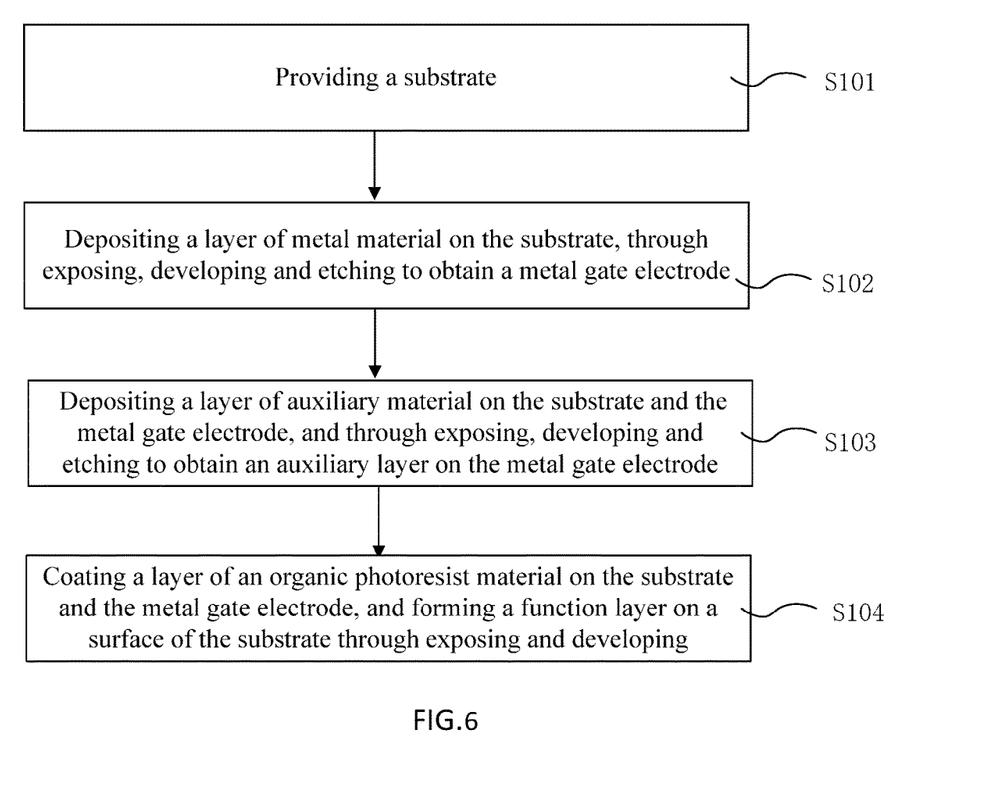
FIG. 6 is a flow chart of a manufacturing method for a material property testing device according to an embodiment of the present invention.

With reference to FIG. 6 and FIG. 1, and FIG. 6 is a flow chart of a manufacturing method for a material property testing device according to an embodiment of the present invention. The method includes:

S101: providing a substrate 100.

Preferably, the substrate 100 can be a transparent glass substrate or a quartz substrate.

S102: depositing a layer of metal material on the substrate 100, through exposing, developing and etching to obtain a metal gate electrode 200.

Wherein, the step of depositing a layer of metal material on the substrate 100 usually adopts a physical deposition or a chemical deposition. Then, coating a layer of photoresist on the metal material layer. Then, according to different exposure amount, through exposing and developing, a photoresist having a size equal to the metal gate electrode is adhered on the metal material, and a surface of the other portion of metal material to be removed is exposed. Then, through etching process to etch the metal material having exposed surface. The metal material protected by the photoresist is remained to form the metal gate electrode 200.

S103: depositing a layer of auxiliary material on the substrate 100 and the metal gate electrode 200, and through exposing, developing and etching to obtain an auxiliary layer 300 on the metal gate electrode 200.

The process of depositing, exposing, developing and etching is the same as the process of forming the metal gate electrode 200, no more repeating. Wherein, the auxiliary layer 300 can only form on the metal gate electrode 200, or include a portion that forms in the substrate 100 and located at a side of the metal gate electrode 200.

S104: coating a layer of an organic photoresist material on the substrate 100 and the metal gate electrode 200, and forming a function layer 400 on a surface of the substrate 100 through exposing and developing.

Wherein, the organic photoresist material is similar to a photoresist used in the step S101. The organic photoresist material is coated on the substrate 100 and the metal gate electrode 200. Then, according to the pattern of the function layer, setting different exposure amount. Then, though exposing and developing, the organic photoresist on the metal gate electrode and other unwanted organic photoresist are removed in order to obtain the function layer having a specific pattern. Specifically, the function layer 400 is a color filter layer for cooperating with a light-emitting device to test a property of a material or including a color filter layer and insulation layer.

Comparing with the conventional art, in the material property testing device obtained by the manufacturing method of the present embodiment, and in the manufacturing process, through forming the auxiliary layer 300 on the metal gate electrode 200, in the forming process of the function layer 400 in the step S104, at the location of the metal gate electrode 200, the organic photoresist is coated on the auxiliary layer 300, and the organic photoresist is not directly contacted with the metal gate electrode 200. Because an adhesion force of the organic photoresist on the auxiliary layer 300 is strong, a film of the organic photoresist being disposed is even such that after exposing and developing, the function layer 400 having an ideal pattern is obtained so as to ensure the testing effect of the material property testing device.

Figure 7:
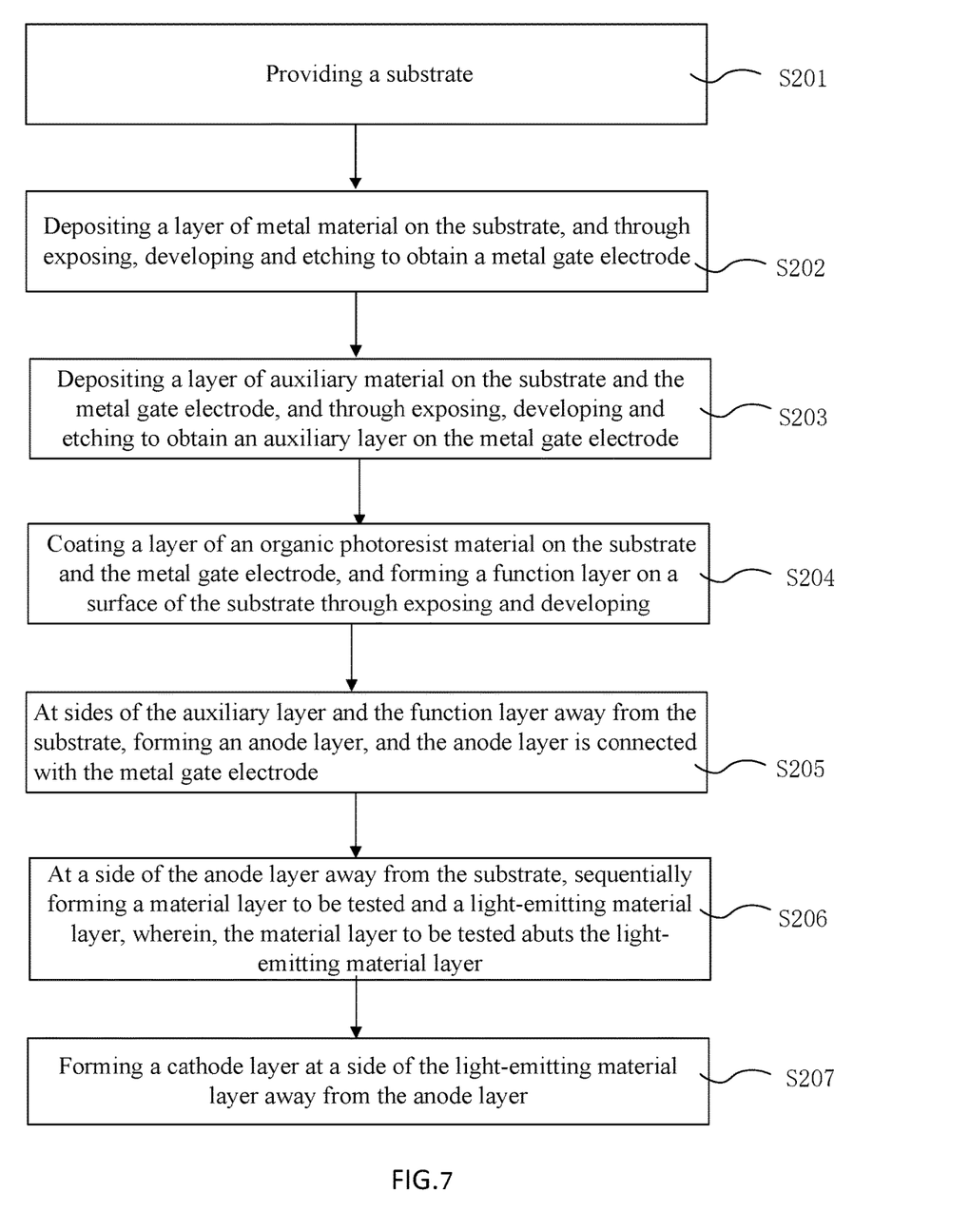
FIG. 7 is a flow chart of a manufacturing method for a material property testing device according to another embodiment of the present invention.

With reference to FIG. 7 and FIG. 4, and FIG. 7 is a flow chart of a manufacturing method for a material property testing device according to another embodiment of the present invention. The method includes:

S201: providing a substrate 100.

S202: depositing a layer of metal material on the substrate 100, through exposing, developing and etching to obtain a metal gate electrode 200.

S203: depositing a layer of auxiliary material on the substrate 100 and the metal gate electrode 200, and through exposing, developing and etching to obtain an auxiliary layer 300 on the metal gate electrode 200.

S204: coating a layer of an organic photoresist material on the substrate 100 and the metal gate electrode 200, and forming a function layer 400 on a surface of the substrate 100 through exposing and developing.

S205: at sides of the auxiliary layer 300 and the function layer 400 away from the substrate 100, forming an anode layer 500, and the anode layer 500 is connected with the metal gate electrode 200.

Wherein, the formation process of the anode layer 500 is the same as the formation process of the metal gate electrode 200, no more repeating.

S206: at a side of the anode layer 500 away from the substrate 100, sequentially forming a material layer to be tested 700 and a light-emitting material layer 600, wherein, the material layer to be tested 700 abuts the light-emitting material layer 600.

Wherein, the material layer to be tested 700 is formed through depositing, exposing, developing and etching. Specifically, depositing a material to be tested on the anode layer 500 first. After exposing and developing, etching at least a portion of the material to be tested on the anode layer 500 in order to reveal the anode layer 500 for evaporating the light-emitting material layer 600. Or, evaporating the light-emitting material layer 600 on the anode layer 500 first, then, depositing the material to be tested on the anode layer 500 and the light-emitting material layer 600. Finally, etching the material to be tested corresponding to the light-emitting material layer 600 in order to prepare for a step S207.

S207: forming a cathode layer 800 at a side of the light-emitting material layer 600 away from the anode layer 500.

Evaporating the light-emitting material layer 600 on the cathode layer 800 through an evaporation method. In another embodiment, the cathode layer 800 can be evaporated to be extended outside a region corresponding to the light-emitting material layer 600. For example, extending to be on the material layer to be tested 700 so that an exterior structure of the entire device is smoother.

Figure 8:
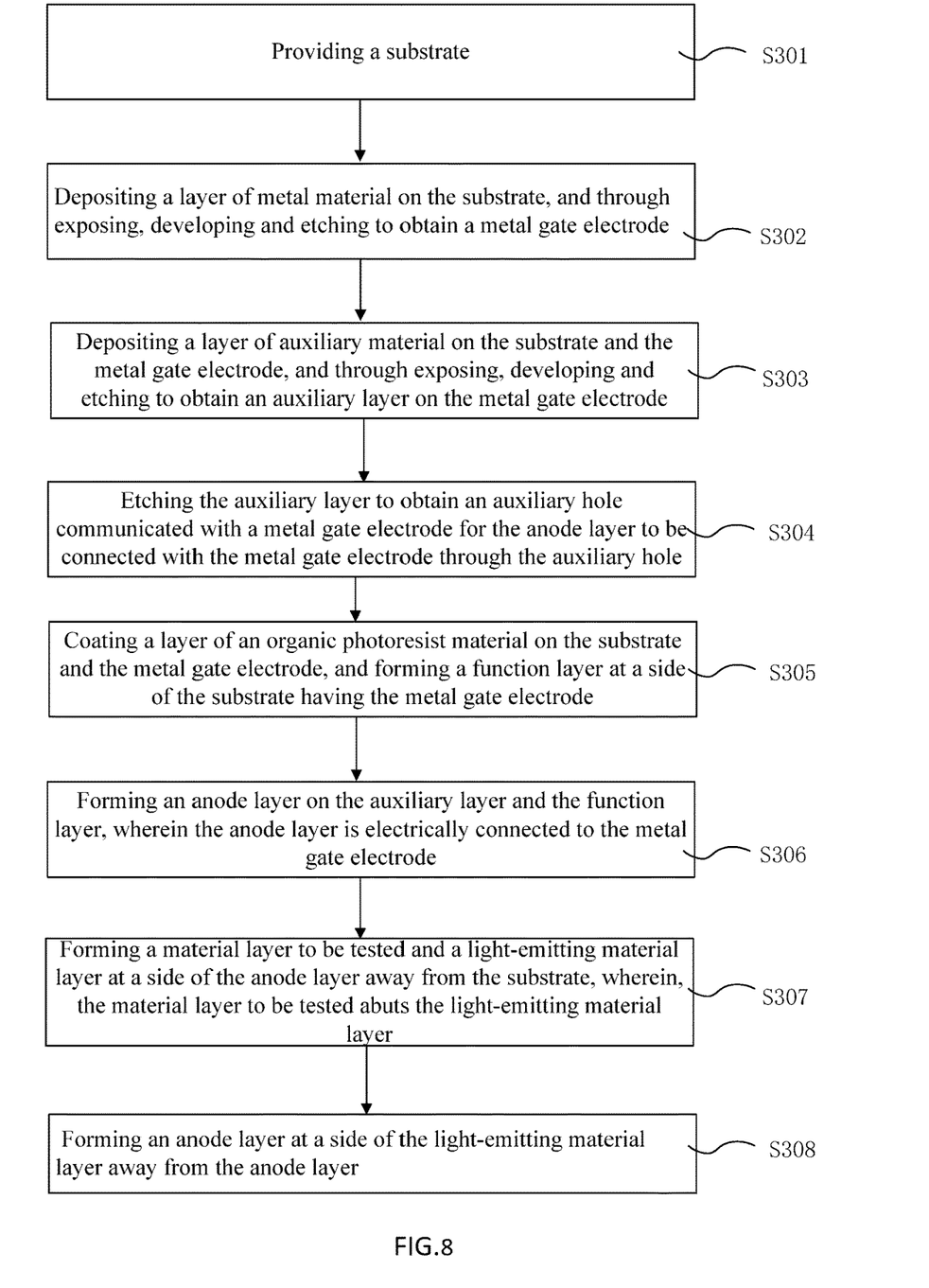
FIG. 8 is a flow chart of a manufacturing method for a material property testing device according to another embodiment of the present invention.

With reference to FIG. 8, FIG. 4 and FIG. 5, and FIG. 8 is a flow chart of a manufacturing method for a material property testing device according to another embodiment of the present invention. The method includes:

S301: providing a substrate 100.

S302: depositing a layer of metal material on the substrate 100, through exposing, developing and etching to obtain a metal gate electrode 200.

S303: depositing a layer of auxiliary material on the substrate 100 and the metal gate electrode 200, and through exposing, developing and etching to obtain an auxiliary layer 300 on the metal gate electrode 200.

S304: etching the auxiliary layer 300 to obtain an auxiliary hole 303 communicated with a metal gate electrode 200 for the anode layer 500 to be connected with the metal gate electrode 200 through the auxiliary hole 303.

In another embodiment, the step of etching the auxiliary layer 300 to obtain an auxiliary hole 303 communicated with a metal gate electrode 200 can be performed after a step of forming a function layer 400. The only requirement is that the above step should be finished before a step S306 for forming an anode layer 500. It can be understood that in another embodiment, the auxiliary hole 303 is not necessary, but leaving a spacing at a side surface of the metal gate electrode 200 for filling the anode layer 500 in the disposition process of the anode layer 500 in order to realize an electric connection between the anode layer 500 and the metal gate electrode 200. Specifically, the spacing can be formed between the side surface of the metal gate electrode 200 and the function layer 400. Or, when the auxiliary layer 300 includes the second body 302 covering on the substrate, the auxiliary hole 303 is etched to be located at a side surface of the metal gate electrode 200 and be located on the second body 302. After the auxiliary hole 303 is formed, the side surface of the metal gate electrode 200 is revealed. That is, using a side surface of the metal gate electrode 200 as an inner wall of the auxiliary hole 303.

S305: coating a layer of an organic photoresist material on the substrate 100 and the metal gate electrode 200, and forming a function layer 400 at a side of the substrate having the metal gate electrode 200.

S306: forming an anode layer 500 on the auxiliary layer 300 and the function layer 400, wherein the anode layer 500 is electrically connected to the metal gate electrode 200.

In the present embodiment, the material for manufacturing the anode layer 500 is filled in the auxiliary hole 303 in order to realize an electric connection between the anode layer 500 and the metal gate electrode 200.

S307: forming a material layer to be tested 700 and a light-emitting material layer 600 at a side of the anode layer 500 away from the substrate 100, wherein, the material layer to be tested 700 abuts the light-emitting material layer 600.

S308: forming an anode layer 800 at a side of the light-emitting material layer 600 away from the anode layer 500.

The above embodiments of the present invention are not used to limit the claims of this invention. Any use of the content in the specification or in the drawings of the present invention which produces equivalent structures or equivalent processes, or directly or indirectly used in other related technical fields is still covered by the claims in the present invention.

What is claimed is:

1. A material property testing device for testing a property of a material, comprising:
   a substrate;
   a metal gate electrode disposed at a side of the substrate;
   an auxiliary layer disposed at a side of the metal gate electrode away from the substrate, wherein, the auxiliary layer includes a first body and a second body, the first body is disposed on the side of the metal gate electrode away from the substrate, and the second body is disposed on a side of the substrate having the metal gate electrode; and
   a function layer including a color filter layer and being disposed on the side of the substrate having the metal gate electrode, the second body is located between the function layer and substrate, in the formation process of the function layer, an organic photoresist is attached on the auxiliary layer for a period of time, and the function layer is used for cooperating with a light-emitting device to test the property of the material.

2. The material property testing device according to claim 1, wherein, the color filter layer is made of acrylic resin.

3. The material property testing device according to claim 1, wherein, the function layer further includes an insulation layer, the color filter layer is disposed between the substrate and the insulation layer.

4. The material property testing device according to claim 1, wherein, the device further includes an anode layer, a material layer to be tested, a light-emitting material layer and a cathode layer, wherein, the anode layer is electrically connected to the metal gate electrode, the material layer to be tested is located between the anode layer and the cathode layer, the material layer to be tested, the anode layer and the cathode layer form a cavity for receiving the light-emitting material layer, the light-emitting material layer is received in the cavity, and the light-emitting material layer abuts the material layer to be tested.

5. A material property testing device for testing a property of a material, comprising:
   a substrate;
   a metal gate electrode disposed at a side of the substrate;

an auxiliary layer disposed at a side of the metal gate electrode away from the substrate; and a function layer including an organic photoresist and being disposed on the side of the substrate having the metal gate electrode, in the formation process of the function layer, the organic photoresist is attached on the auxiliary layer for a period of time, and the function layer is used for cooperating with a light-emitting device to test the property of the material;

wherein the function layer includes a color filter layer.

6. The material property testing device according to claim 5, wherein, the auxiliary layer includes a first body and a second body, the first body is disposed on the side of the metal gate electrode away from the substrate, and the second body is located between the function layer and the substrate.

7. The material property testing device according to claim 5, wherein, the color filter layer is made of acrylic resin.

8. The material property testing device according to claim 5, wherein, the function layer further includes an insulation layer, the color filter layer is disposed between the substrate and the insulation layer.

9. The material property testing device according to claim 5, wherein, the device further includes an anode layer, a material layer to be tested, a light-emitting material layer and a cathode layer, wherein, the anode layer is electrically connected to the metal gate electrode, the material layer to be tested is located between the anode layer and the cathode layer, the material layer to be tested, the anode layer and the cathode layer form a cavity for receiving the light-emitting material layer, the light-emitting material layer is received in the cavity, and the light-emitting material layer abuts the material layer to be tested.

10. The material property testing device according to claim 9, wherein, the auxiliary layer is provided with at least one auxiliary hole communicating with the metal gate electrode, and the anode layer is electrically connected to the metal gate electrode through the auxiliary hole.

11. A manufacturing method for a material property testing device, comprising steps of:

providing a substrate;

depositing a layer of metal material on the substrate, through exposing, developing and etching to obtain a metal gate electrode;

depositing a layer of auxiliary material on the substrate and the metal gate electrode, through exposing, developing and etching to obtain an auxiliary layer on the metal gate electrode;

coating a layer of an organic photoresist material on the substrate and the metal gate electrode, and forming a function layer on a side of the substrate having the metal gate electrode through exposing and developing;

at sides of the auxiliary layer and the function layer away from the substrate, forming an anode layer, and the anode layer is electrically connected with the metal gate electrode;

at a side of the anode layer away from the substrate, sequentially forming a material layer to be tested and a light-emitting material layer, wherein, the material layer to be tested abuts the light-emitting material layer; and forming a cathode layer at a side of the light-emitting material layer away from the anode layer.

12. The manufacturing method for a material property testing device according to claim 11, wherein, before the step of at sides of the auxiliary layer and the function layer away from the substrate, forming an anode layer, the method further comprises a step of etching the auxiliary layer to obtain an auxiliary hole communicated with a metal gate electrode for the anode layer to be connected with the metal gate electrode through the auxiliary hole.

\* \* \* \* \*